(12) United States Patent
Kahana et al.

(10) Patent No.: US 6,485,434 B1
(45) Date of Patent: Nov. 26, 2002

(54) APPARATUS FOR ACOUSTIC PERCUSSION OF A BODY

(76) Inventors: Doron Kahana, 5509 S. Kimbark Ave., Chicago, IL (US) 60637; Alon Kahana, 5107 S. Blackstone Apt #1203, Chicago, IL (US) 60615; Emanuel Kahana, 5509 S. Kimbark Ave., Chicago, IL (US) 60637

( * ) Notice: Subject to any disclaimer, the term of this patent is extended or adjusted under 35 U.S.C. 154(b) by 57 days.

(21) Appl. No.: 09/609,802

(22) Filed: Jul. 3, 2000

(51) Int. Cl.$^7$ ................................................ A61B 5/00
(52) U.S. Cl. ..................... 600/552; 600/586; 128/897
(58) Field of Search ....................... 600/552, 553, 600/586, 587, 593; 128/897, 898; 381/67, 77, 111, 151; 340/573.1, 573.2, 573.3, 392.1, 384.2; 367/197–199

(56) References Cited

U.S. PATENT DOCUMENTS

| | | | | |
|---|---|---|---|---|
| 4,067,253 A | * | 1/1978 | Wheelwright et al. | 84/687 |
| 5,109,421 A | * | 4/1992 | Fox | 381/333 |
| 5,287,099 A | * | 2/1994 | Tsunoda | 340/7.62 |
| 5,633,473 A | * | 5/1997 | Mori et al. | 84/625 |
| 5,913,834 A | * | 6/1999 | Francais | 600/591 |
| 6,198,407 B1 | * | 3/2001 | Koga | 340/7.58 |

* cited by examiner

*Primary Examiner*—Kevin Shaver
*Assistant Examiner*—Charles Marmor, II

(57) ABSTRACT

An apparatus for acoustic percussion of the human and animal body, the apparatus including an oscillator circuit for creating electrical signals for exciting a loudspeaker and producing sound waves; a waveform shaping circuit for shaping the electrical signals created by the oscillator into a waveform; an amplifier circuit for amplifying the signals shaped by the waveform shaper to the level required by the loudspeaker; a loudspeaker for producing sound waves when excited by the electrical signals created by the oscillator and shaped by the waveform shaper; a potentiometer to control the waveform rate created by the waveform shaper; a potentiometer to control the tone produced by the oscillator; and a potentiometer to control the volume of the sound produced by the loudspeaker. A preferred embodiment includes a battery for powering the apparatus, an activating mechanism, and a case or container for packaging the components of the apparatus.

9 Claims, 1 Drawing Sheet

APPARATUS FOR ACOUSTIC PERCUSSION OF A BODY

BACKGROUND OF THE INVENTION

This invention relates generally to the field of medical diagnostics devices, and more particularly to an apparatus for acoustic percussion of the human and animal body. The difference between an ultrasound machine and this apparatus is that the apparatus of the instant invention uses sound waves in the audible range, and the detection is via an acoustic detector/amplifier (stethoscope), again in the audible range. Changes in the quality of sound (pitch, echo, etc.) reflect a solid-fluid-air transition.

Acoustic percussion is a well-known method for detecting internal organs and structures, air-fluid levels, air-fluid-solid transitions, and bone density. It is performed manually, by knocking with the finger on a specific location on the body, and listening to the echo. Experienced physicians can perform preliminary diagnostics using this method.

The shortcomings of manual percussion have to do with physical attributes (e.g. small fingers, lack of strength, poor dexterity), with difficulty of diagnosis, and with inconsistent force application in performing manual percussion. Moreover, both hands are needed in order to perform manual percussion; thus, a stethoscope cannot be used simultaneously. Electronic percussion can be done with one hand, freeing the other hand to listen with a stethoscope. This allows for greater diagnostic accuracy, especially in obese patients, for whom manual percussion is obscure and imprecise. Physicians are often reluctant to refer obese patients to ultrasound just for liver/spleen evaluation, especially due to cost management efforts and time constraints. Therefore, the aid of an electronic percussion apparatus not only will assist the physician, but will also lower medical cost, while enhancing the medical care provided to the patient.

SUMMARY OF THE INVENTION

The primary object of the invention is to provide a mean to ease the detection and evaluation in a human and animal body, of internal organs and structures, air-fluid levels, air-fluid-solid transitions, and bone density.

Another object of the invention is to help the detection of the above in body locations when manual percussion does not work.

Another object of the invention is to help the detection of the above for physicians who have limitations in their ability to perform manual percussion.

According to a preferred embodiment of the present invention, there is provided an apparatus for acoustic percussion of a body, said apparatus comprises an electronic circuit, performing as an oscillator, creating electrical signals capable of exciting a loudspeaker, and producing sound waves; an electronic circuit, performing as a waveform shaper for the electrical signals created by said oscillator, shaping the said electrical signal in a form of a waveform; an electronic circuit, performing as an amplifier for the electrical signals shaped by said waveform shaper, amplifying the signals to the level required by the loudspeaker; a loudspeaker, producing sound waves when excited by said electrical signals created by said oscillator, and shaped by said waveform shaper; a potentiometer or other control means, to control waveform rate created by said waveform shaper; a potentiometer or other control means, to control the tone produced by said oscillator; and a potentiometer or other control means, to control the volume of the sound produced by said loudspeaker.

Other objects and advantages of the present invention will become apparent from the following descriptions, taken in connection with the accompanying drawings, wherein, by way of illustration and example, an embodiment of the present invention is disclosed.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Figure 1:
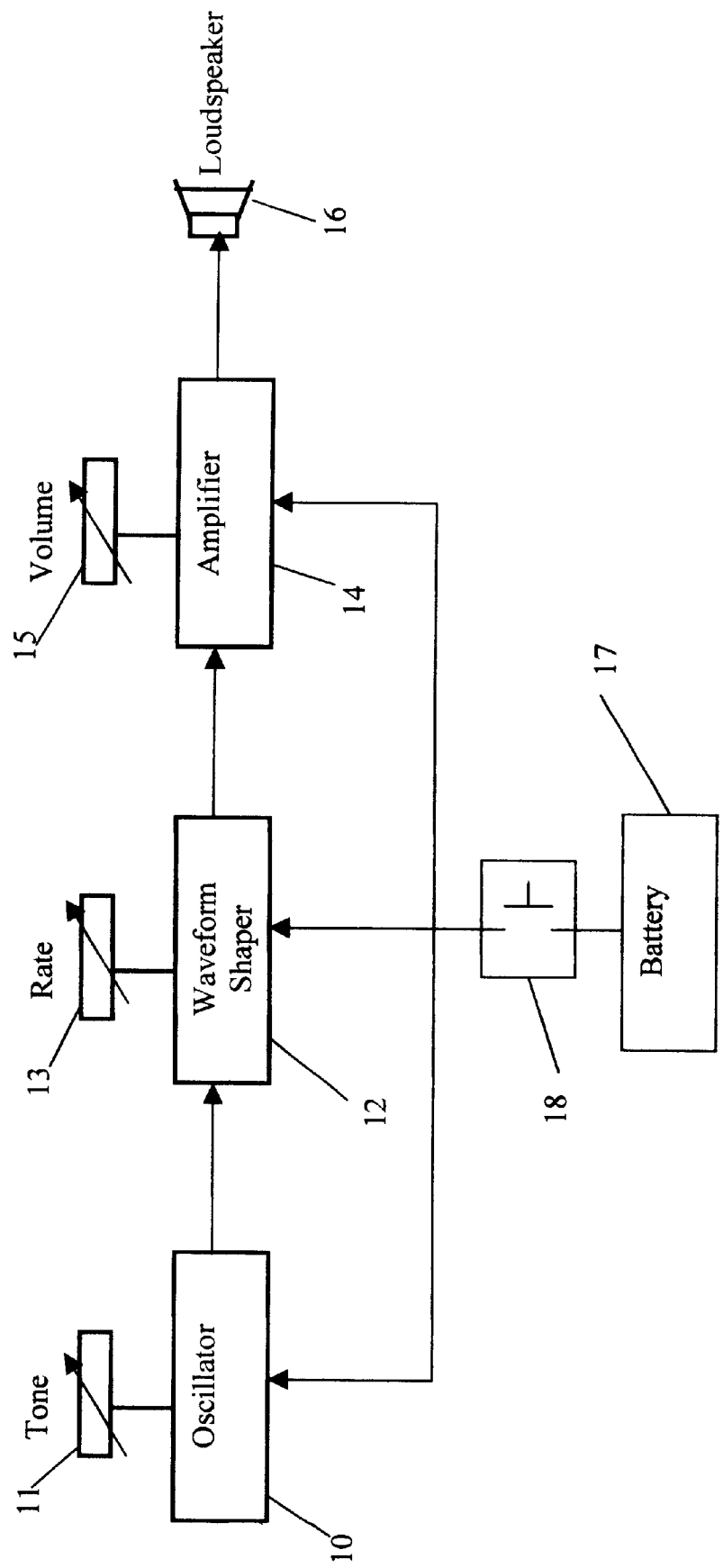
FIG. 1 is a schematic block diagram of the apparatus.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

In accordance to the present invention, FIG. 1 shows a block diagram of the apparatus, comprising electronic circuits. An electrical signal in the acoustic range of frequencies is generated by oscillator 10. The tone (frequency) of the signal is controlled by potentiometer 11. The output from the oscillator is then transferred to circuit 12, called a waveform shaper. The waveform shaper forms pulses with the electrical signal, whose rate is controlled by potentiometer 13. The output from the waveform shaper is transferred to an amplifier 14, which amplifies the signal to the proper volume level. The volume level is controlled by potentiometer 15. Finally, the output of the amplifier is fed to a loudspeaker 16, which produces sound waves. The apparatus is powered by a battery 17 or other means of power supply. Activation of the apparatus is accomplished by a means of activation 18. A case or container is provided for housing the components of the apparatus.

In the practice of the invention, the apparatus is used by setting the loudspeaker in touch with the skin, in the vicinity of the part of the body being examined, and listening to the echo with the help of a stethoscope, or other listening device. The changes in the echo for various settings of the apparatus indicate the location of internal organs and structures, air-fluid levels, air-fluid-solid transitions, and bone percussion, in the human and animal body. It is found in practice that the precise settings of the apparatus, the stethoscope, and the apparatus controls, depends on the specific use and characteristics of the body being examined.

Although a preferred embodiment of the method and apparatus of the present invention has been illustrated in the accompanying Drawings and described in the foregoing Detailed Description, it is understood that the invention is not limited to the embodiment disclosed, but is capable of numerous rearrangements, modifications, and substitutions without departing from the spirit of the invention as set forth and defined by the current claims.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An apparatus for detecting and evaluating internal organs and structures, air-fluid levels, air-fluid-solid transitions, and bone density, said apparatus comprising:

means for providing acoustic percussion to a human or animal body, said means for providing acoustic percussion comprising:

oscillator means for creating electrical signals capable of exciting a loudspeaker and producing sound waves;

waveform shaper means for shaping said electrical signals created by said oscillator means into a waveform;

amplifier means for amplifying the signals shaped by the waveform shaper means to the level required by the loudspeaker;

means for producing sound waves when excited by said electrical signals created by said oscillator means and shaped by the said waveform shaper means;

means for controlling waveform rate created by said waveform shaper means;

means for controlling a tone produced by said oscillator means;

means for controlling a volume of the sound produced by said loudspeaker;

means for powering said apparatus; and means for activating said apparatus.

2. The apparatus recited in claim 1, wherein said oscillator means comprises an electronic circuit.

3. The apparatus recited in claim 1, wherein said waveform shaper means comprises an electronic circuit.

4. The apparatus recited in claim 1, wherein said amplifier means comprises an electronic circuit.

5. The apparatus recited in claim 1, wherein said means for producing sound waves comprises a loudspeaker.

6. The apparatus recited in claim 1, wherein said means for controlling waveform rate comprises a potentiometer.

7. The apparatus recited in claim 1, wherein said means for controlling tone comprises a potentiometer.

8. The apparatus recited in claim 1, wherein said means for controlling volume comprises a potentiometer.

9. The apparatus recited in claim 1, wherein said means for powering said apparatus comprises a battery.

* * * * *